United States Patent [19]
Treacy

[11] Patent Number: 5,716,362
[45] Date of Patent: Feb. 10, 1998

[54] PATELLA MILLING INSTRUMENT

[75] Inventor: Patrick J. Treacy, Towaco, N.J.

[73] Assignee: Howmedica Inc., New York, N.Y.

[21] Appl. No.: 604,048

[22] Filed: Feb. 20, 1996

[51] Int. Cl.$^6$ .................................................. A61B 17/56
[52] U.S. Cl. ........................... 606/87; 606/80; 606/88; 269/6
[58] Field of Search .................. 606/80, 87, 88, 606/79, 102; 269/6, 214, 169, 170, 171.5

[56] References Cited

U.S. PATENT DOCUMENTS

| | | | |
|---|---|---|---|
| 4,220,322 | 9/1980 | Hobday | 269/214 |
| 4,663,862 | 5/1987 | Petersen | 606/88 |
| 4,721,104 | 1/1988 | Kaufman et al. | 606/88 |
| 4,893,801 | 1/1990 | Flinn | 269/6 |
| 5,108,401 | 4/1992 | Insall et al. | 606/87 |
| 5,129,908 | 7/1992 | Petersen | 606/88 |
| 5,147,365 | 9/1992 | Whitlock et al. | 606/88 |
| 5,222,955 | 6/1993 | Mikhail | 606/80 |
| 5,284,482 | 2/1994 | Mikhail | 606/86 |
| 5,417,695 | 5/1995 | Axelson, Jr. | 606/89 |
| 5,486,177 | 1/1996 | Mumme et al. | 606/79 |
| 5,575,793 | 11/1996 | Carls et al. | 606/88 |

*Primary Examiner*—Michael Buiz
*Assistant Examiner*—Julian W. Woo
*Attorney, Agent, or Firm*—Peter C. Richardson; Lawrence C. Akers; Raymond W. Augustin

[57] ABSTRACT

A patella milling instrument has a planar base with a fixed patellar clamping element formed thereon. A movable patellar milling element is slidably mounted on the base and is movable towards and away from the fixed clamping element. A drive element is operable between the base and the movable element for moving the movable clamping element. The drive element is actuated by a drive mechanism fixed in a handle of the device found at one end thereof and connected to a drive element which is also in the form of a ratchet element. A movable end mill type cutting element is mounted on a support arm supported by the base. The support arm is capable of movement in directions parallel to the plane of the base and is adjustable in a direction perpendicular to the base. The end mill has a drive shaft rotatably mounted in a bushing in an end of the support arm which drive shaft is rotatable by a power tool and capable of movement in a direction perpendicular to the plane of the base.

19 Claims, 7 Drawing Sheets

PATELLA MILLING INSTRUMENT

BACKGROUND OF THE INVENTION

1. Field of the Invention

The invention relates to a patella milling instrument which allows the surgeon to accurately define the depth and plane of a patella resection while maintaining visibility during the cut to prepare a patella by both insetting and resurfacing techniques to receive a prosthetic implant. More particularly, it relates to a patella clamp which positions the patella underneath a moveable milling tool mounted on the clamp.

2. Description of the Prior Art

Prior art devices for aiding the surgeon in performing patella resections are well known to those skilled in the art. For example, Peterson, in U.S. Pat. No. 4,663,862, teaches a method and instruments for the installation of a patella button prosthesis which involves performing a patella resection.

In particular, Peterson describes a saw guide which comprises a pliers-like instrument having a pair of mutually pivotable jaw members. The jaw members are designed so as to enable them to surround the outer periphery of the patella with each jaw member having a respective handle, integrally formed therewith, which handles may be pivoted so as to pivot the jaw members to and from engagement with the patella periphery. At the ends of the handles a locking device is provided which enables the locking of the jaw members about the patella periphery. The Peterson device requires that a flat saw blade be guided over the face of the jaw members after the patella has been set to the correct depth between the members.

U.S. Pat. No. 5,147,365 discloses a patella osteotomy guide in which the jaw members include a slot for guiding the flat saw blade and an arm for setting the saw blade depth in the patella.

Milling instruments are known in the preparation of the femur for a prosthetic implant. One such milling system is disclosed in U.S. Pat. No. 4,721,104 in which the area between the condyles of a femur is shaped. U.S. Pat. No. 5,417,695 shows the use of a milling instrument to prepare the condylar area of a femur prior to receiving an implant.

U.S. Pat. No. 5,486,177 discloses a patella milling instrument having a clamp which contacts the underside of the patella. A similar clamping tool is shown in U.S. Pat. No. 5,284,482.

U.S. Pat. No. 5,222,955 shows a reaming system designed to cut a conical bore in a patella surface while the patella is being held in a patella clamp similar to that disclosed in U.S. Pat. No. 5,284,482.

SUMMARY OF THE INVENTION

It is an object of the invention to provide an easy to use and mechanically simple patella milling instrument which allows a very accurate resection of the patella to be repeatedly performed.

It is a further object of the invention to provide a patella milling instrument that allows accurate resections to be performed over a predetermined range of prespecified resection depths.

It is yet an additional object of the invention to provide a patella milling instrument which allows the surgeon to easily view the resection while it is being performed.

It is still a further objection of the invention to provide a patella milling instrument which allows an end mill mounted thereon to be moved in both directions along the plane of the resection guide and along an axis perpendicular to the plane of the resection guide.

These objects are accomplished by a patella milling instrument having a base component on which clamps are mounted to contact and hold the edge of the patella while it is being milled to accept the implant. In a typical resurfacing operation, the entire patella articulating surface is milled flat. In addition, it is possible to provide a cylindrical inset in the patella leaving a wall of bone to support the prosthetic implant which is then placed in the inset bore and then usually cemented therein.

The clamping device is comprised of a fixed clamping member and a movable clamping member. The movable clamping member slides along the plane of the base member and is actuated or driven to clamp and hold the patella by squeezing and compressing a trigger on the base member. The clamp remains locked on the patella until a release is actuated, allowing the movable clamp to be backed off the patella to thereby release it.

The movable clamp may be mounted on rails formed on the surface of the base member of the instrument. These rails reference the anterior, i.e., non-articulating side of the patella to establish the depth of the cut and the resulting thickness of the patella after milling as well as the plane of the cut.

A ratchet drive mechanism is located on the base member and is actuated by the trigger in a manner similar to a caulking gun.

A depth stop component is affixed to a calibration post extending perpendicularly outwardly from the plane of the base member of the milling instrument to allow the surgeon to easily set the amount of bone remaining after the cut. This depth stop component is set to the proper depth before the milling tool is attached to an arm supported by the calibrated post. Once the arm is placed in the proper calibration with respect to the post, the surgeon needs only to seat the miller in a bushing on the arm to provide the proper patella thickness. The bushing surrounds a drive shaft on the milling tool and is oriented along an axis parallel to the axis of the post. The depth stop component also accepts a gauge which allows the surgeon to visualize where the plane of the resection on the articular side of the patella will be.

The milling tool is comprised of a drive shaft and a replaceable cutter blade and may be of any standard type such as that shown in U.S. Pat. No. 5,486,177. For the resurfacing of the patella, one diameter blade on one size shaft may be utilized to prepare any size patella. The end mill for the insetting technique is also comprised of one drive shaft but has several diameter cutters to form a bore in the patella. This bore may be located anywhere in the patella by moving the support arm along either of the two directions of the plane of the base member.

Specifically, the patella milling instrument comprises a planar (generally flat) base member having a fixed clamping element formed adjacent one end thereof and a moveable clamping element slidably mounted on the base member. An actuation or drive mechanism is provided between the base member and the movable clamping element for moving the movable clamping element towards the fixed clamping element and thereby capture the patella therebetween. A support arm is fixed to the base member for supporting a milling tool above an area of the base member between the fixed and movable clamping elements. At one end the support has an axial bore therein for engaging a drive shaft on the milling tool to permit rotation of the tool about the axis of the drive shaft and also to allow the movement of the milling tool in the axial direction of the bore. The bore may be lined with a bushing.

The patella milling instrument includes a handle formed at one end of the base with a trigger mechanism movable to advance a ratchet drive element mounted within the base of the milling instrument. The patella milling instrument drive element has ratchet teeth thereon or may use a wedge or screw action and is capable of moving the movable clamping element towards the fixed clamping element. The support arm extends generally in a direction parallel to the base plane and is supported on the base by a post extending along an axis generally perpendicular to the plane of the base member. The support arm may be rotatably mounted on the post for rotation about the axis perpendicular to the plane of the base member. The arm may also be movable towards and away from the post to allow movement of the milling tool parallel to the plane of the base. The post has calibrations to indicate the distance of the arm and therefore the milling tool from the surface of the planar base member. The planar base member clamping elements have teeth which extend in a direction generally parallel to the plane of the base member to engage the periphery of the patella. A release is provided so that the clamping elements may be disengaged from the patella after milling a planar surface or an inset or hole in the patella for the prosthetic patellar implant.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
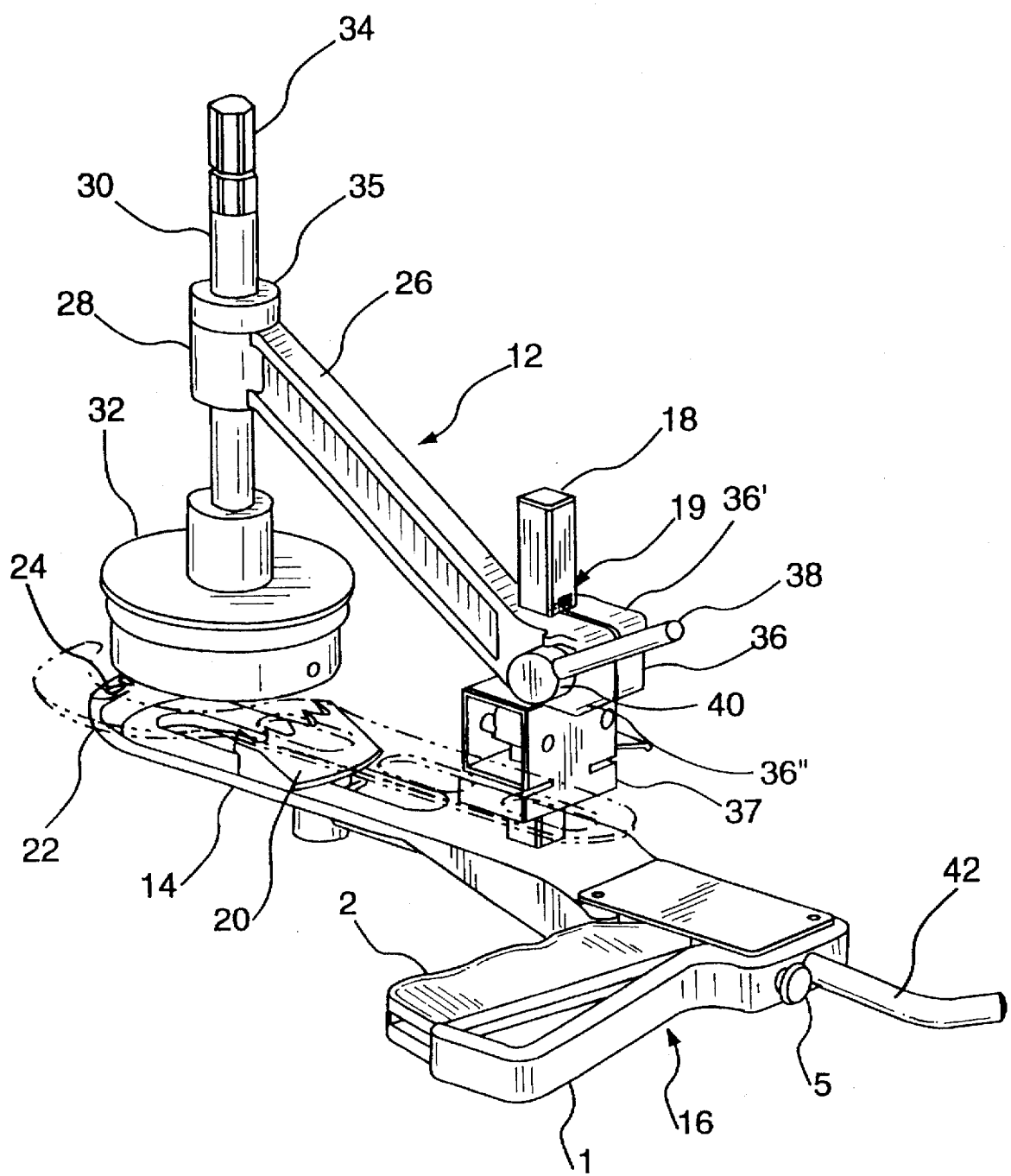
FIG. 1 is an isometric view of the patella milling instrument.
Figure 2:
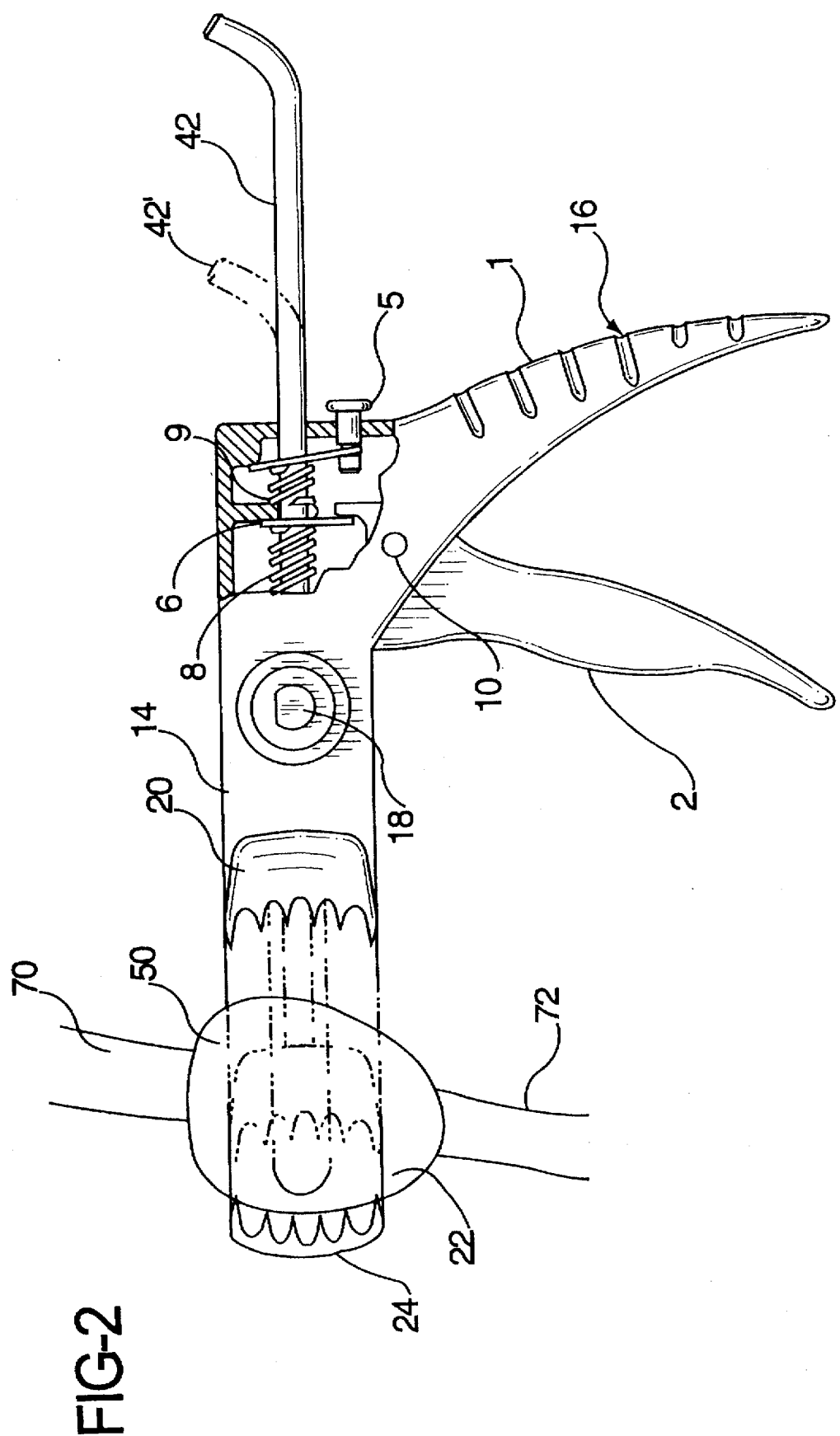
FIG. 2 is a top view of the patella milling instrument shown in FIG. 1 with a patella positioned above the clamping surface thereon.

Referring to FIG. 1 there is shown a patella milling guide of the present invention generally denoted as 12 which includes a generally planar base member 14 having a handle assembly 16 at one end thereof. The planar base member includes a post 18 extending generally perpendicularly therefrom which post has calibrations 19 thereon. A clamping element 20 is slidably mounted on the base member 14 for movement towards the end 22 thereof opposite the end with handle 16. End 22 includes teeth 24 for clamping onto the periphery of a patella as seen in FIG. 2.

A milling tool support arm 26 is slidably mounted on post 18 and has a drive holder 28 at the end of arm 26 opposite post 18. Drive holder 28 may include a bushing (not shown) to act as a bearing for the rotation of shaft 30 of milling tool 32. A drive motor or drill body (not shown) attaches to end 34 of shaft 30 causing milling tool 32 to rotate about the axis of drive holder 28. Milling tool 32 may also be moved upwardly and downwardly with respect to the surface of the planar base member 14 of patella milling instrument 12. Stop 35 is used to limit movement of shaft 30 towards base member 14.

Arm 26 may be locked vertically with respect to the planar base member 14 along post 18 by clamping mechanism 36 which is actuated by a typical locking handle 38. Handle 38 can be rotated so that a screw attached to base 40 thereof may pull arms 36' and 36" together to thereby clamp arm 26 to post 18.

Clamping element 20 is rigidly connected to drive shaft 42 so that it can be moved towards or away from end 22 with clamping elements 24. Handle 16 contains an actuation mechanism either in the form of a ratchet or a wedge, as best seen in FIG. 2, which is used to actuate or move shaft 42.

Referring to FIG. 2, there can be seen a partial cutaway view of the preferred actuation mechanism which causes drive shaft 42 to be moved towards the patella 50 and thereby clamp the same between clamping elements 20 and 24.

Handle portion or trigger 2 pivots around pin 10 which is mounted in fixed handle portion 1, causing wedge 6 to act against spring 8 and force shaft 42 towards end 22 of the clamping device. Locking spring 9 acts against stop plate 7 when handle 2 is returned to its non-actuating position to thereby lock shaft 42 against movement away from end 22. Shaft 42 can be advanced any required distance by the repeated actuation of trigger handle 2. When it is necessary to release patella 50 after the milling operation is completed, release 5 is actuated which disengages locking plate 7.

Figure 3:
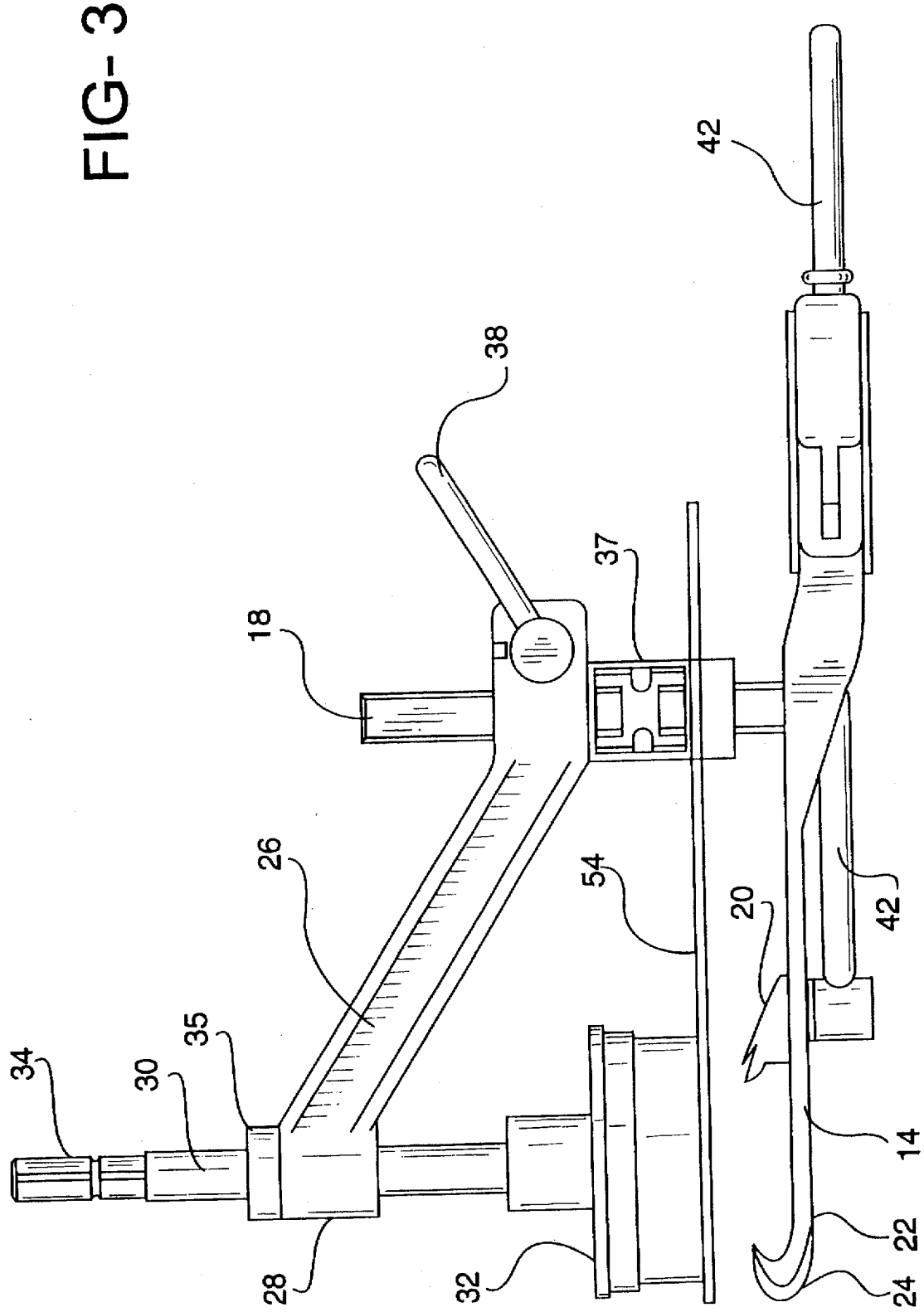
FIG. 3 is a side elevation view of the patella milling instrument shown in FIGS. 1 and 2.

Referring to FIG. 3 there is shown a side view of the clamp 12 shown in FIG. 1. Depth stop box 37 may be positioned with respect to calibration 19 to delineate the amount of bone remaining on patella 50 after milling. The positioning of box 37 sets the position of drive holder 28. During assembly, arm 26 is placed on post 18 and brought into contact with the top of box 37 to accurately set final position of milling tool 32. The distance between the face of milling tool 32 and stop 35 is factory set to produce the thickness read on post 18.

An optional plane gauge 54 is shown which allows the surgeon to visualize the depth and plane of resection. The plane gauge is attached to post 18 via box 37 to allow the surgeon to easily visualize the amount of bone remaining after the cut.

Figure 4:
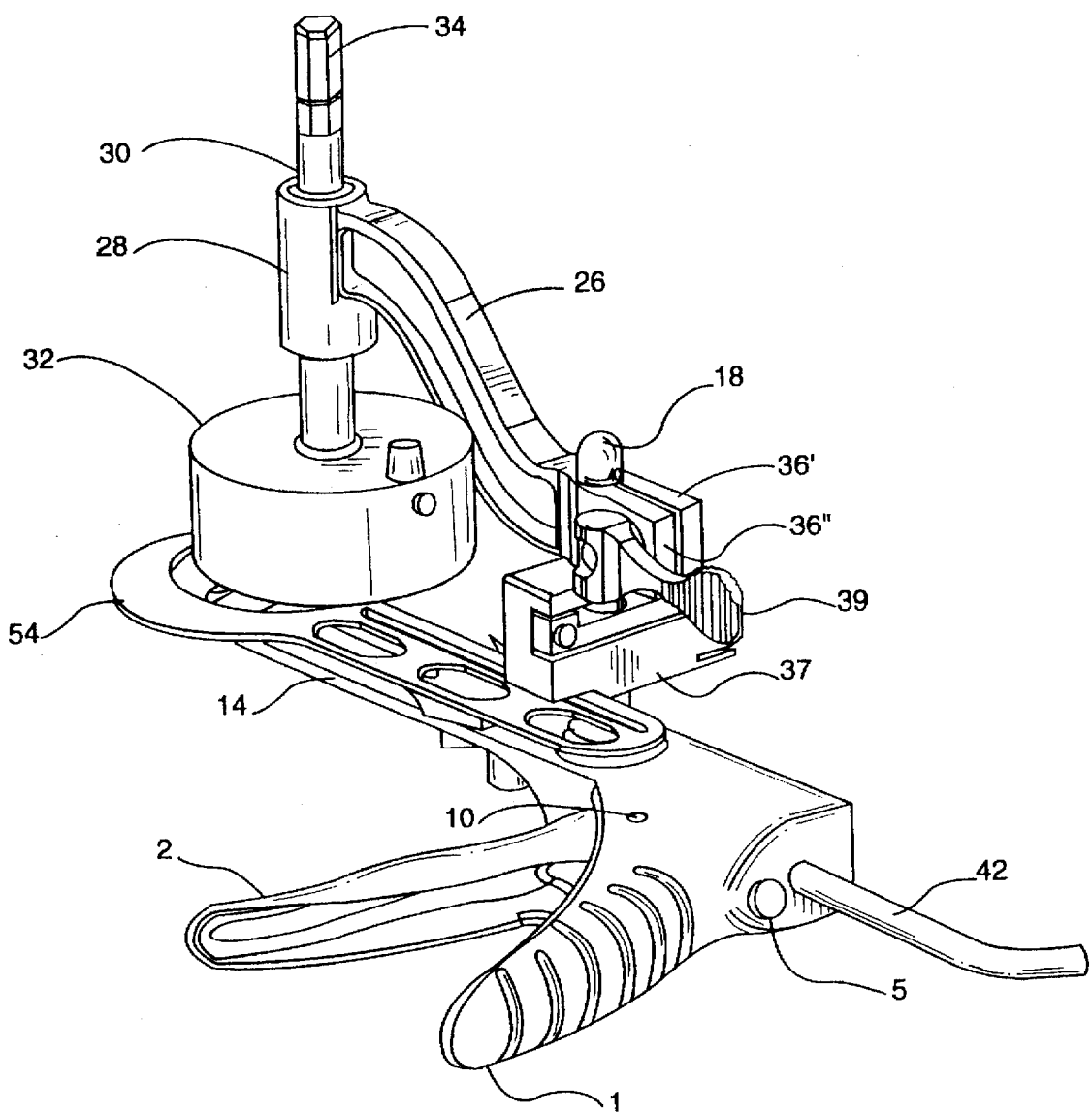
FIG. 4 is an isometric view of an alternate embodiment of the patella milling instrument of the present invention.
Figure 5:
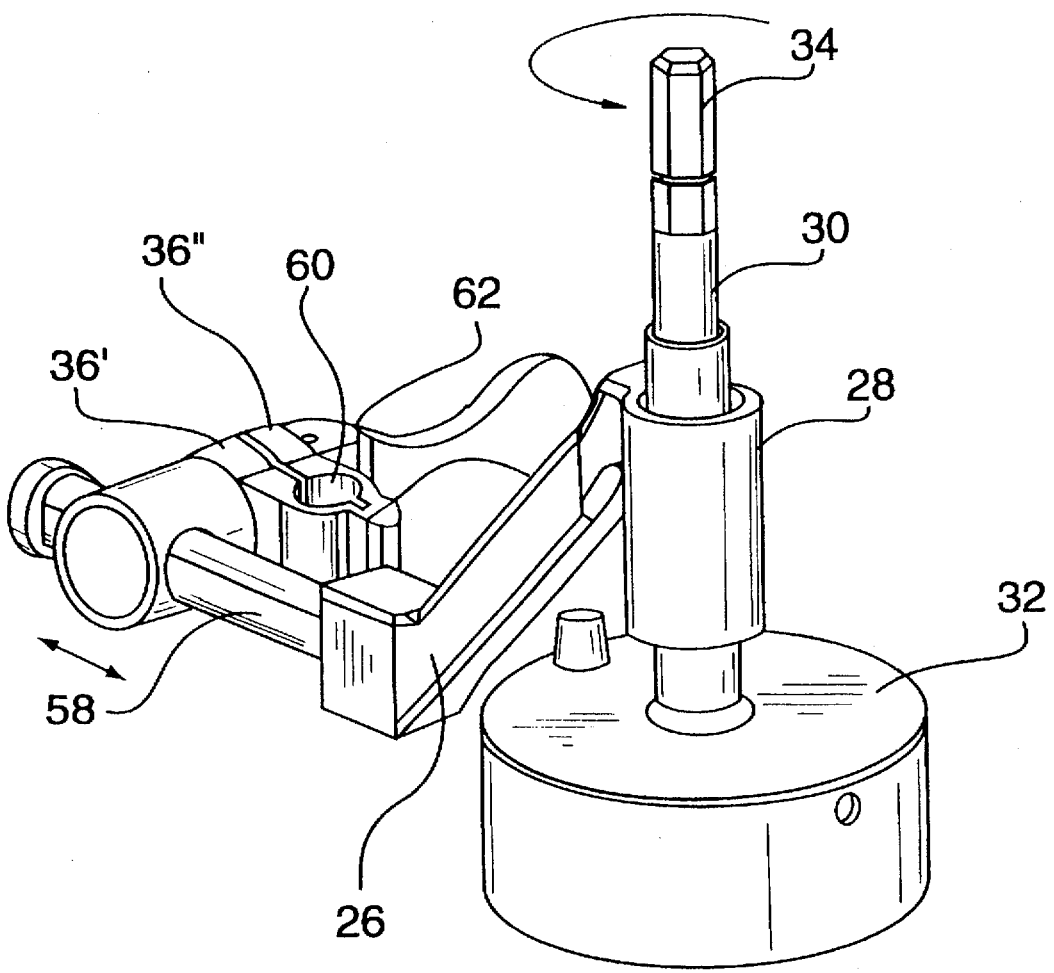
FIG. 5 is an isometric view of the patella milling portion of yet another alternate embodiment of the present invention.

An alternate embodiment is shown in FIG. 4 with the only difference being post 18 is circular or D-shaped so that arm 26 can now rotate in an arc along a plane parallel to the plane of base member 14. An alternate method of locking arm 26 to post 18 is shown in which a camming action is used to bring portions 36' and 36" together by the actuation of handle 39. Referring to FIG. 5 there is shown an alternate embodiment of arm 26 in which milling tool 32 may be moved towards and away from post 18 via sliding arm 58.

In the embodiment of FIG. 5 bore 60 engages cylindrical post 18. When D-shaped in cross-section, post 18 will still allow rotation when engaged with circular bore 60, but could also engage a D-shaped opening 60 in arm 26 if rotation prevention was desired.

Preferably, the clamping mechanism 62 of FIG. 5 allows arm 26 to be locked rotationally onto post 18 and also simultaneously locks arm 58, if desired, thereby preventing it from further movement toward or away from end 22 of the milling instrument 12.

Figure 6:
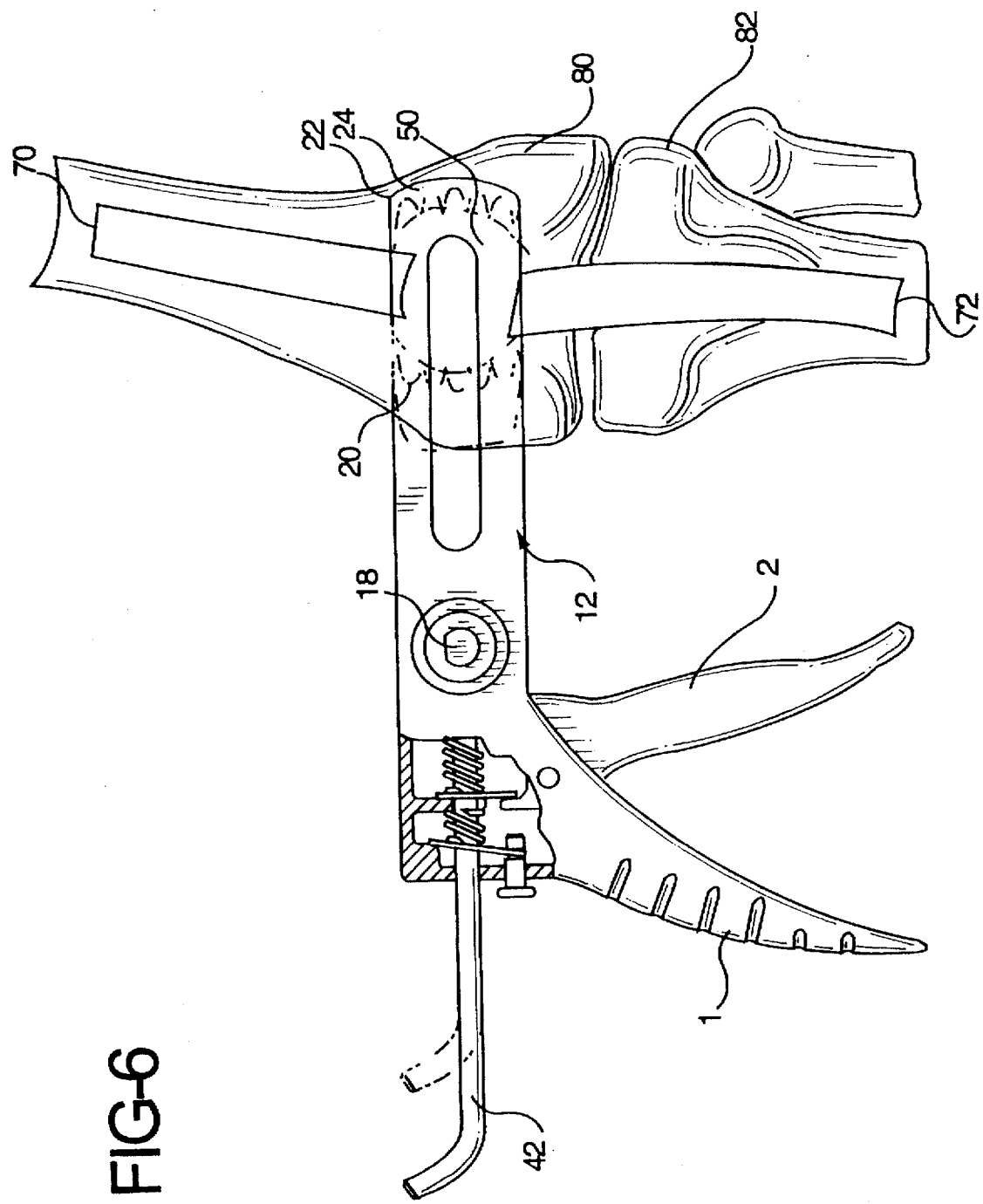
FIG. 6 is a plan view of the patella instrument of FIG. 2 mounted on a patella with the working surface thereon facing posteriorly.

Referring to FIG. 6 there is shown patella milling instrument 12 initially engaging patella 50 which is attached to femur 80 and tibia 82 by ligaments 70,72. In this position clamps 20,24 and post 18 face posteriorly.

Figure 7:
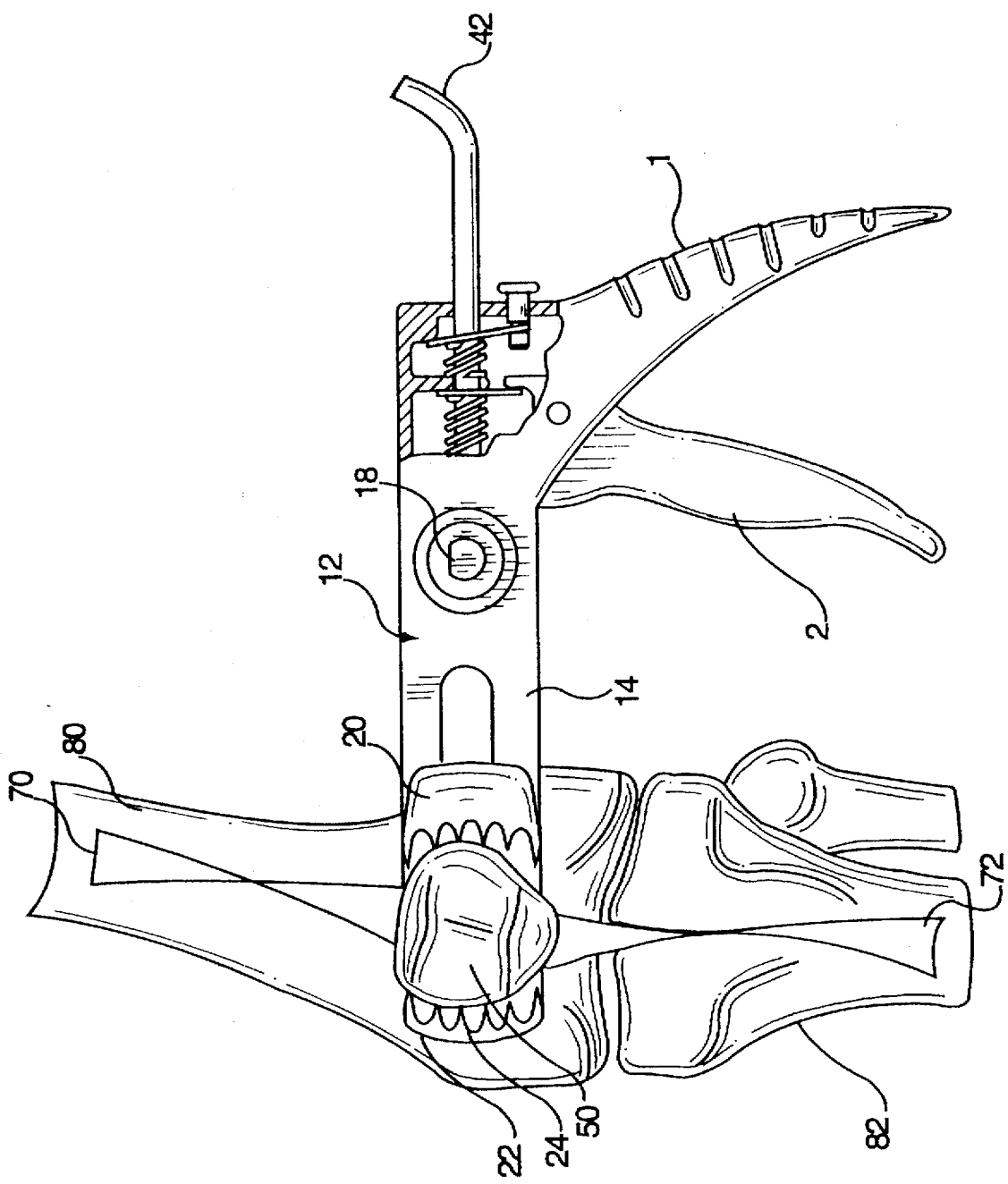
FIG. 7 is a plan view of the patella instrument of FIG. 2 after being flipped in the medial-lateral direction so that the working surface thereof and the posterior surface of the patella are exposed.

As shown in FIG. 7 the patella 50 is flipped over in the medial-lateral direction using instrument 12 so that the anterior face of patella 50 points posteriorly and clamps 20,24 face anteriorly. Arm 26 with milling tool 32 is then mounted on post 18 so that the surgical procedure discussed below may be performed.

The surgical technique to utilize the patella milling instrument 12 of the present invention is very straight forward and allows the surgeon increased visibility over prior art devices. Initially, the surgeon determines the location of the depth stop box 37, he then places the clamp on the patella which is attached about the knee by tendons 70 and 72 from the anterior side of the patella, i.e., with clamps 20 and 24 facing posteriorly. Clamp 20 is advanced by the action of trigger 2 and shaft 42 to secure patella 50 against clamp 24. The instrument is then flipped in the medial-lateral direction to expose the posterior surface of the patella. Arm 26, including milling tool 32, is then attached to post 18 and locked in position against the face of depth stop box 37. The power device is attached to end 34 of the milling tool and the patella is milled to the level established by stop 35.

The same procedure as described above can be used to inset or cut a bore (not shown) in patella 50 for placement of a prosthetic patella. Obviously, a smaller diameter milling tool 32 is required for this operation.

While several examples of the present invention have been described, it is obvious that many changes and modifications may be made thereunto, without departing from the spirit and scope of the invention.

I claim:

1. A patella milling instrument comprising:
   a generally planar base having a fixed patella clamping element formed thereon;
   a moveable patella clamping element slidably mounted on said base and moveable towards and away from said fixed clamping element for engaging a peripheral surface of said patella;
   a drive element operable between said base and said moveable element for moving said moveable clamping element; and
   a moveable cutting element mounted on a support arm supported by said base, said support arm positioning said cutting element in an area of said planar base between said fixed and said moveable clamping elements and allowing said cutting element to move in a direction perpendicular to the plane of said planar base.

2. The patella milling instrument as set forth in claim 1 wherein said base member has a handle formed on an end thereof.

3. The patella milling instrument as set forth in claim 2 wherein said handle includes a moveable trigger portion with a drive element thereon.

4. The patella milling instrument as set forth in claim 3 wherein said drive element has a ratchet element thereon operatively engaging a trigger ratchet drive element so that said moveable clamping element moves towards said fixed clamping element.

5. The patella milling instrument as set forth in claim 1 wherein said support arm extends in a direction parallel to said base and is supported on said base member by a post extending along an axis perpendicular to the plane of said base member.

6. The patella milling instrument as set forth in claim 5 including means for rotatably mounting said arm on said post for rotation about said axis perpendicular to the plane of said planar base member.

7. The patella milling instrument as set forth in claim 6 wherein said means for rotatably mounting said support arm on said post is a cylindrical bushing.

8. The patella milling instrument as set forth in claim 6 wherein said means for rotatably mounting said arm on said post includes means for moving said arm in a direction parallel to said planar base member.

9. The patella milling instrument as set forth in claim 6 wherein said post has calibrations thereon indicating distances above a surface of said planar base and wherein said means for rotatably mounting said arm on said post includes means for allowing movement of said arm with respect to said post in an axial direction along said axis.

10. The patella milling instrument as set forth in claim 1 wherein said moveable cutting element is an end mill rotatably supported in a bushing on an end of said arm for rotation about an axis perpendicular to the plane of said planar base member.

11. The patella milling instrument as set forth in claim 1 wherein each of said moveable and fixed clamping elements includes teeth extending in a direction generally parallel to said planar base member to grip the patella.

12. A patella milling instrument comprising:
   a base member having a fixed clamping element formed adjacent one end thereof;
   a moveable clamping element slidably mounted on said base member;
   an actuation mechanism for moving said movable clamping element towards said fixed clamping element for engaging a peripheral surface of the patella; and
   a support fixed to said base member for supporting a milling tool above an area of said base member between said fixed and said moveable clamping elements, said support having an axial bore therein for engaging a drive shaft on said milling tool to permit rotation of said tool about the axis of said axial bore and movement of said tool along said axis.

13. The patella milling instrument as set forth in claim 12 wherein said base member has a handle formed on an end thereof.

14. The patella milling instrument as set forth in claim 13 wherein said handle includes a moveable trigger portion with a drive element thereon.

15. The patella milling instrument as set forth in claim 14 wherein said support extends in a direction parallel to said base and is supported on said base member by a post extending along an axis perpendicular to the plane of said base member.

16. The patella milling instrument as set forth in claim 12 wherein said support extends in a direction parallel to said base and is supported on said base member by a post extending along an axis perpendicular to the plane of said base member.

17. The patella milling instrument as set forth in claim 16 wherein said post has calibrations thereon indicating distances above a surface of said planar base and wherein said means for rotatably mounting said arm on said post includes means for allowing movement of said arm with respect to said post in an axial direction along said axis.

18. The patella milling instrument as set forth in claim 12 wherein said milling tool an end mill rotatably supported in a bushing on an end of said arm for rotation about an axis perpendicular to the plane of said planar base member.

19. The patella milling instrument as set forth in claim 12 wherein each of said moveable and fixed clamping elements includes teeth extending in a direction generally parallel to said planar base member to grip the patella.

* * * * *